(12) United States Patent
Gan

(10) Patent No.: US 10,980,526 B2
(45) Date of Patent: Apr. 20, 2021

(54) HOOK AND FENESTRATION RETRACTOR

(71) Applicant: LIVAC IP CO PTY LTD, Toorak (AU)

(72) Inventor: Philip Gan, Warrnambool (AU)

(73) Assignee: LIVAC IP CO PTY LTD, Toorak (AU)

( * ) Notice: Subject to any disclaimer, the term of this patent is extended or adjusted under 35 U.S.C. 154(b) by 264 days.

(21) Appl. No.: 16/097,753

(22) PCT Filed: May 3, 2017

(86) PCT No.: PCT/AU2017/000098
§ 371 (c)(1),
(2) Date: Oct. 30, 2018

(87) PCT Pub. No.: WO2017/190177
PCT Pub. Date: Nov. 9, 2017

(65) Prior Publication Data
US 2020/0383674 A1    Dec. 10, 2020

(30) Foreign Application Priority Data
May 3, 2016 (AU) ................. 2016901631

(51) Int. Cl.
*A61B 17/02* (2006.01)
*A61B 17/34* (2006.01)
*A61B 17/00* (2006.01)

(52) U.S. Cl.
CPC ...... *A61B 17/0218* (2013.01); *A61B 17/3423* (2013.01); *A61B 2017/00526* (2013.01); *A61B 2017/0287* (2013.01)

(58) Field of Classification Search
CPC .... A61B 2017/0287; A61B 2017/0225; A61B 2017/0281
See application file for complete search history.

(56) References Cited

U.S. PATENT DOCUMENTS 5,582,577 A    12/1996    Lund et al.
5,785,649 A  *  7/1998    Fowler, Jr. ......... A61B 17/0293
                                                 600/217
(Continued)

FOREIGN PATENT DOCUMENTS

CN    104114105 A    10/2014
DE    102010000789 A1    7/2011
(Continued)

OTHER PUBLICATIONS

English language translation of KR 2009-0030815 A; accessed using EPO Patent Translate on Sep. 22, 2020.*
(Continued)

*Primary Examiner* — Julianna N Harvey
(74) *Attorney, Agent, or Firm* — McKee, Voorhees & Sease, PLC

(57) ABSTRACT

A surgical device for retraction of a body part is disclosed. The surgical device comprises an anchor at each end of the surgical device; an elongate body comprising a plurality of fenestrations along a body length wherein each fenestration is sized to receive at least part of one of the anchors; and a stopper preventing a tail end of the device being pulled through any of the plurality of fenestrations. The surgical device may also comprise additional features such as, the elongate body being sufficiently flexible to fold back or partly fold back on itself and the lead anchor and tail anchor being oriented in the same direction. Also provided is a method of manufacturing the surgical device; a method for inserting the surgical device; and a kit comprising the surgical device.

17 Claims, 9 Drawing Sheets

(56) References Cited

U.S. PATENT DOCUMENTS

| | | | | |
|---|---|---|---|---|
| 5,964,698 A | * | 10/1999 | Fowler | A61B 17/02 24/130 |
| 6,824,511 B1 | * | 11/2004 | Bell | A61B 17/02 600/227 |
| 8,251,889 B2 | | 8/2012 | Scott | |
| 9,480,470 B2 | | 11/2016 | Roberts | |
| 2005/0159711 A1 | * | 7/2005 | Kathrani | A61B 17/3421 604/264 |
| 2011/0040152 A1 | * | 2/2011 | Kim | A61B 17/0218 600/206 |
| 2013/0109924 A1 | | 5/2013 | Gan | |
| 2014/0235936 A1 | | 8/2014 | Baas et al. | |

FOREIGN PATENT DOCUMENTS

| | | | |
|---|---|---|---|
| KR | 20090030815 A | * | 3/2009 |
| KR | 20090030815 A | | 3/2009 |
| WO | 2014004654 A1 | | 1/2014 |

OTHER PUBLICATIONS

LIVAC IP Co Pty Ltd, PCT/AU2017/000098 filed May 3, 2017, Extended European Search Report, 6 pages, dated Nov. 26, 2019.

\* cited by examiner

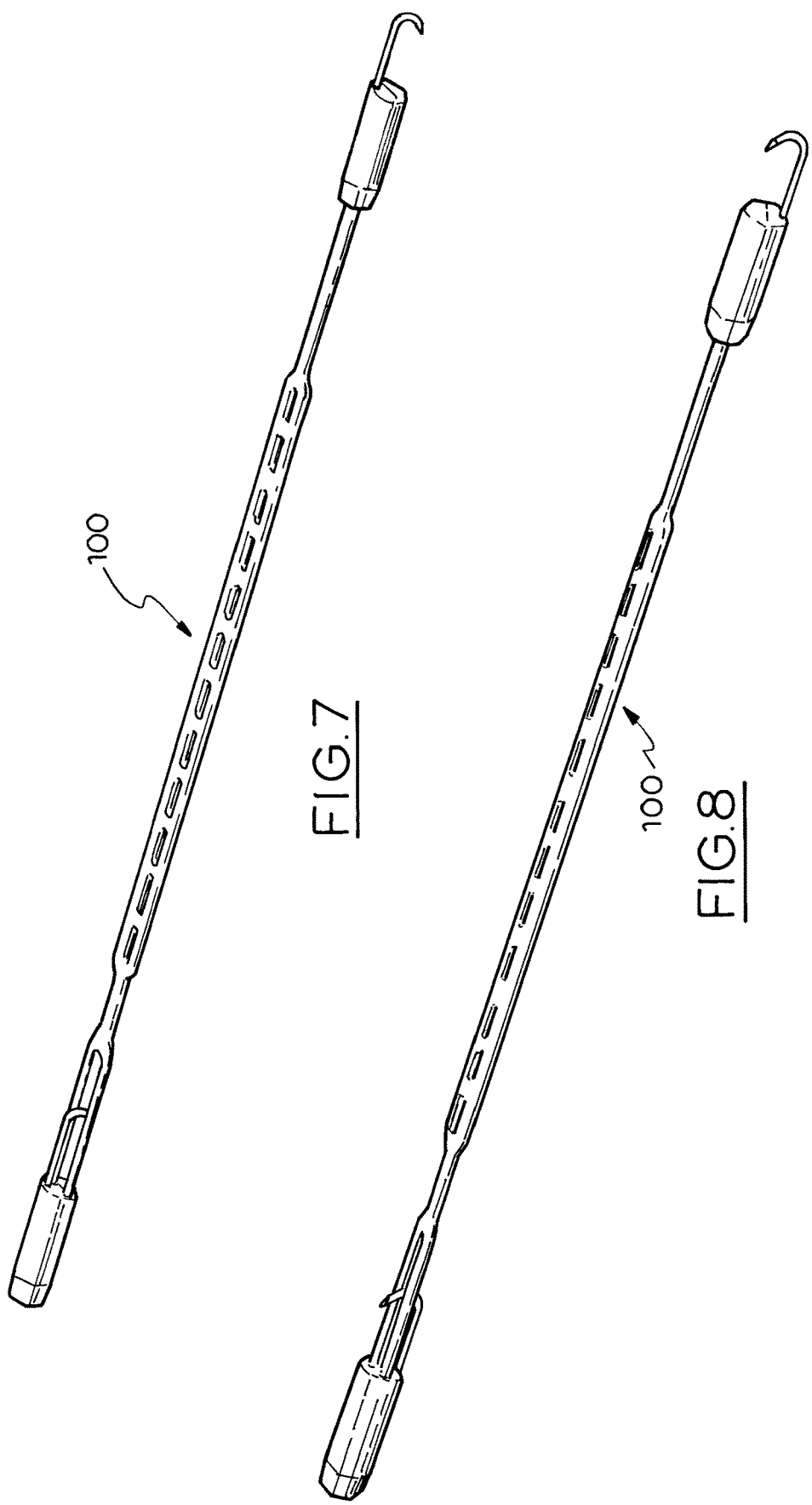

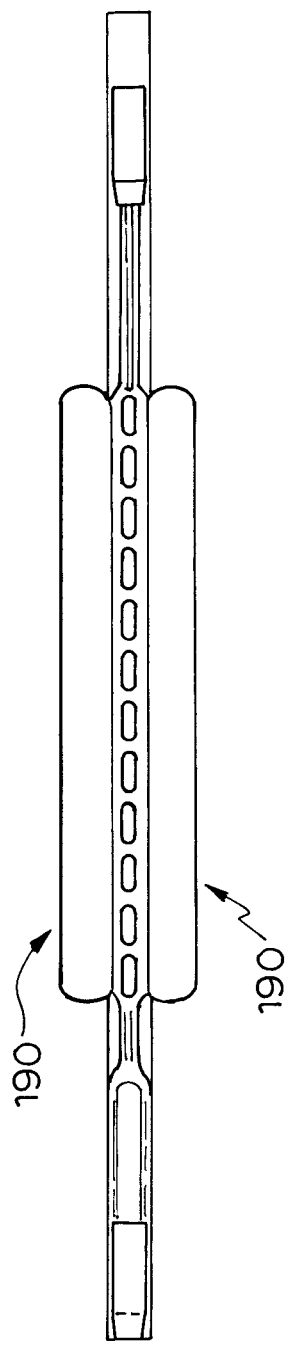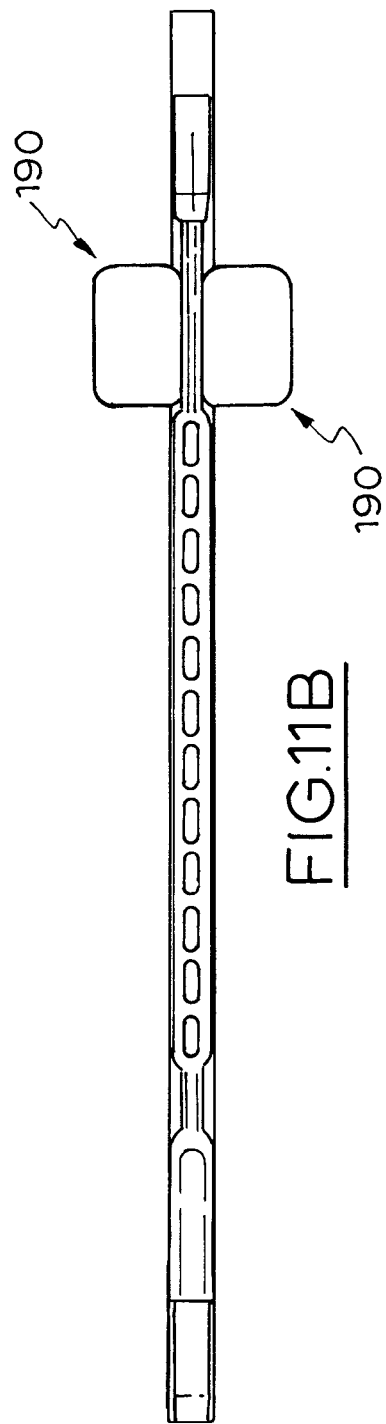

HOOK AND FENESTRATION RETRACTOR

FIELD OF THE INVENTION

The present invention relates to a surgical device, a method of using a surgical device and a method of manufacturing a surgical device. More particularly, this invention relates to a surgical device and methods for retracting a body part during surgery comprising an anchor at each end and an elongate body comprising a plurality of fenestrations.

BACKGROUND TO THE INVENTION

Laparoscopic surgery is carried out by passing ports through multiple small incisions, or by using Single Port Laparoscopic Surgery (SPLS) which utilizes only a single incision and single port with multiple channels. The benefits of laparoscopic surgery and/or SPLS have been reported to include reduced post-operative pain, tissue trauma and scarring as well as faster recovery from surgical procedures.

In accessing target tissue to be operated upon, medical personnel typically use a retractor system or apparatus to hold adjacent tissue to be retracted from the operating field. This is particularly the case where the laparoscopic procedure is carried out in the abdomen of a patient and obstructive tissue needs to be temporarily and gently moved out of the way. Such retractors may be inserted into the abdomen and retained in position through an incision or laparoscopic port, however some are designed to be entirely intra-abdominal. These typically comprise variations on a theme of a thread, tube, band or rod with an anchoring mechanism such as a clasp or surgical hook on either end. Some designs comprise two segments with an anchor between them as well as at each end. Patients and their internal organs can vary dramatically in size and shape, hence these internal retractors need to incorporate mechanisms to vary the length between the two (or more) anchoring points. These mechanisms may include a lockable pulley system, or, where a needle on a thread attached to the retractor is passed through the abdominal wall, the point at which the thread is secured externally can be varied. A similar means of retraction can also be attained by using surgical sutures, anchored at one point, drawn across the organ to be retracted, then anchored at a second point. Pulley systems can be fiddly to manipulate, and when tightening a thread which is already applying a force against the retracted organ, such as liver, there is a risk of causing "cheese-wiring" as the thread drags across the tissue. Internal retractors which have a threaded end on a needle, which is passed through the abdominal wall, are limited by the ensuing difficulty in adjusting to an alternative location once the needle has been passed.

U.S. Pat. No. 8,251,889 discloses an apparatus for intra-abdominally moving an internal organ comprising a length of cord that has one tissue connector at each end and one in its mid-section. The tissue connectors may be suture needles, "T" bars, surgical graspers, barbed needles, hooks, clasps or rivet assemblies.

Another device to provide retraction of larger soft tissue structures is the EndoLift™ Port-Free Retractor. The EndoLift™ Retractor and organ are anchored directly to the endocavity wall. The device is comprised of a telescopic stainless steel bar and two articulated clips positioned on either end of the bar. The stainless steel bar is placed underneath the tissue and then an instrument is used to grasp one of the clips and anchor it to the intra-abdominal wall. The process of fastening the second clip creates the lift necessary to retract the tissue.

US patent publication 2014/0235936, the publication of U.S. patent application Ser. No. 14/346,703, discloses a system for retracting an organ comprising two clips joined by a flexible string or thread. Each clip comprises two generally opposing segments that form a jaw that can be opened and closed to grab tissue.

A retractor which can be secured at a desired length without using a pulley mechanism or externalised suture, and yet which is completely intra-abdominal, would be advantageous, and could complement or enhance other forms of retraction, such as a vacuum retractor apparatus.

SUMMARY OF THE INVENTION

The present invention is broadly directed to a novel and inventive surgical device and method which has particular application in laparoscopic surgery but is not limited thereto. The invention has arisen after the present inventor developed a method and device for adjusting the length or span between two anchors which does not rely upon a pulley system, nor externalising of any suture anchor.

In a broad form, the invention relates to a retractor comprising an anchor at each end and an elongate body comprising a plurality of fenestrations along a body length.

In a first aspect, there is provided a surgical device for retraction of a body part comprising:
 an anchor at each end of the surgical device;
 an elongate body comprising a plurality of fenestrations along a body length wherein each fenestration is sized to receive at least part of one of the anchors; and
 a stopper preventing a tail end of the device being pulled through any of the plurality of fenestrations.

The elongate body may comprise a lead end and a tail end. The elongate body may comprise a strip shape or substantially a strip shape. In other embodiments, the elongate body may comprise a round, ovoid or other shape. The elongate body may be substantially planar in cross sectional profile.

The elongate body may comprise a top surface and a bottom surface. The top and bottom surfaces may be flat or substantially flat. The elongate body may comprise rounded edges between the top and bottom surfaces. The elongate body may comprise side rims. The side rims may comprise a thickness of 2.0 to 3.0 mm; 2.2 to 2.6 mm; or 2.3 to 2.5 mm. The thickness may comprise 2.0; 2.1; 2.2; 2.3; 2.4; 2.5; 2.6; 2.7; 2.8; 2.9 or 3.0 mm. In a particular embodiment, the thickness is 2.4 mm.

The elongate body may comprise a width of 2.0 to 50.0 mm; 4.0 to 25.0 mm or 5.0 to 20.0 mm. The width may comprise 2.0; 2.5; 3.0; 3.5; 4.0; 4.5; 5.0; 5.1; 5.2; 5.3; 5.4; 5.5; 5.6; 5.7; 5.8; 5.9; 6.0; 6.1; 6.2; 6.3; 6.4; 6.5; 6.6; 6.7; 6.8; 6.9; 7.0; 7.1; 7.2; 7.3; 7.4; 7.5; 7.6; 7.7; 7.8; 7.9; 8.0; 8.1; 8.2; 8.3; 8.4; 8.5; 8.6; 8.7; 8.8; 8.9; 9.0; 9.1; 9.2; 9.3; 9.4; 9.5; 9.6; 9.7; 9.8; 9.9; 10.0; 10.1; 10.2; 10.3; 10.4; 10.5; 10.6 10.7; 10.8; 10.9; 11.0; 11.1; 11.2; 11.3; 11.4; 11.5; 11.6; 11.7; 11.8; 11.9; 12.0; 12.1; 12.2; 12.3; 12.4; 12.5; 12.6; 12.7; 12.8, 12.9; 13.0; 13.1; 13.2; 13.3; 13.4; 13.5; 13.6; 13.7; 13.8; 13.9; 14.0; 14.1; 14.2; 14.3; 14.4; 14.5; 14.6; 14.7; 14.8; 14.9; 15.0; 15.5; 16.0; 16.5; 17.0; 17.5; 18.0; 18.5; 19.0; 19.5; 20.0; 20.5; 21.0; 21.5; 22.0; 22.5; 23.0; 23.5; 24.0; 24.5; 25.0; 25.5; 26.0; 26.5; 27.0; 27.5; 28.0 28.5; 29.0; 29.5; 30.0 30.5; 31.0; 32.0; 33.0; 34.0; 35.0; 36.0; 37.0; 38.0; 39.0; 40.0; 41.0; 42.0; 43.0; 44.0; 45.0; 46.0; 47.0; 48.0; 49.0; or 50.0 mm. In one particular embodiment, the width is 4.5 mm. In another particular embodiment, the width is 6.5 mm.

The elongate body may comprise a textured surface or a partially textured surface. The textured or partially textured surface may be comprised on part or all of the elongate body. The part of elongate body comprising a textured or partially textured surface may comprise one or more of the fenestration section; spacer; insert; linker; or anchor retaining section. The textured surface may be provided to increase friction.

The plurality of fenestrations may be arranged in series along the body length of a fenestration section of the elongate body. Each of the plurality of fenestrations may comprise an elongate shape. The elongate shape may be oval, rectangular, or any other shape. Each fenestration may be large enough to receive at least part of one of the anchors. Each fenestration may be membranous such that the fenestration membrane can be penetrated by one or each of the anchors.

Each of the plurality of fenestrations may be defined by a reinforcement. The reinforcement may comprise a bordering section of thickened material. Neighbouring reinforcements may abut each other or may be continuous with each other. The reinforcement may comprise a thickness of 2.0 to 4.0 mm; 2.2 to 3.0 mm; or 2.3 to 2.5 mm. The thickness may comprise 2.0; 2.1; 2.2; 2.3; 2.4; 2.5; 2.6; 2.7; 2.8; 2.9; 3.0; 3.1; 3.2; 3.3; 3.4; 3.5; 3.6; 3.7; 3.8; 3.9; or 4.0 mm. In a particular embodiment, the thickness is 2.4 mm.

The elongate body may comprise one or more wall between neighbouring one or more fenestrations of the plurality of fenestrations. The wall may be thinner than the reinforcement. The wall may comprise a thickness of 0.5 to 5.5 mm; 0.7 to 4.0 mm; or 0.8 to 3.0 mm. The thickness may comprise 0.5; 0.6; 0.7; 0.8; 0.9; 1.0; 1.1; 1.2; 1.3; 1.4; 1.5; 1.6; 1.7; 1.8; 1.9; 2.0; 2.1; 2.2; 2.3; 2.4; 2.5; 2.6; 2.7; 2.8; 2.9; 3.0; 3.1; 3.2; 3.3; 3.4; 3.5; 3.6; 3.7; 3.8; 3.9; 4.0; 4.1; 4.2; 4.3; 4.4; 4.5; 4.6; 4.7; 4.8; 4.9; or 5.0 mm. In one particular embodiment, the thickness is 1.0 mm. In another particular embodiment, the thickness is 2.4 mm.

The elongate body may comprise one or more spacer between the plurality of fenestrations and the anchors. The one or more spacer may comprise one or both of an insert and one or more leash. The one or more spacer may comprise one or both of a lead spacer and tail spacer.

The elongate body may further comprise one or more linkers to attach to each respective anchor. Each of the one or more linkers may comprise a clip.

Each of the one or more spacer may comprise a circular, ovoid, hexagonal or composite cross-sectional profile.

The elongate body may comprise one or more anchor retaining section. The one or more anchor retaining section may comprise a lead end anchor retaining section and a tail end anchor retaining section. Each of the anchor retaining sections may comprise an appropriate thickness for the anchors to be inserted therein. The anchors may be inserted in parallel with the elongate body, at an angle or offset from parallel. The anchor retaining section may comprise a one-way attachment for receiving the anchor.

Each anchor retaining section may comprise a thin flat segment and a thicker base. The thin flat segment may be suitable for grasping. The thicker base may be suitable for retaining an anchor.

In a particular embodiment, the elongate body is sufficiently flexible to fold back or partly fold back on itself to allow at least a part of an anchor to pass through a fenestration.

In another embodiment, one or both of the anchors may comprise a complementary one-way attachment to be received in the anchor retaining section one-way attachment. The one-way attachment and complementary one-way attachment may comprise a male and female attachment.

Each anchor may comprise or consist of a hook. The hook may comprise an elongate segment, a curved segment, a point segment and a point. The elongate section may comprise one or more retainers. Each of the one or more retainers may comprise a coil or one or more barb. The hook may curve in the plane of the elongate body, or at an angle to the elongate body. The hook may curve perpendicularly to the plane of the elongate body. The curved segment may comprise a 180° turn so the point extends parallel to the elongate segment. The elongate segment may be linear or may comprise one or more bend.

The stopper may comprise a region of the elongate body or anchor bigger than at least one of the plurality of fenestrations. The stopper may be comprised on one or both anchors and/or at one or both ends of the elongate body. The stopper may be comprised on a lead anchor or a tail anchor or at only one end of the elongate body.

In another embodiment, the stopper may comprise one or more branches or protrusions comprised on the elongate body or one or each of the anchors. The one or more branches may extend from the elongate segment of the hook or the elongate body. The stopper may be comprised on a lead anchor or a tail anchor or at one end of the elongate body.

The stopper may be comprised on one or both anchor retaining section.

The at least a part of one of the anchors received in the fenestration may comprise the point segment.

The tail anchor point may be flat against, perpendicular, substantially perpendicular, extend obliquely, or extend at any angle to the elongate segment of the tail hook or to the elongate body.

The anchor at each end may comprise a lead anchor and a tail anchor. The lead anchor may comprise a guard. The guard may comprise a stem, an attachment point, a bend and a cap.

In a particular embodiment, the lead anchor and tail anchor are oriented in the same direction.

In another embodiment the anchors may comprise one or more of a tissue clasp, a suture needle, a "T" bar, a surgical grasper, a barbed needle, a clasp or a rivet assembly.

The elongate body may comprise a channel to accommodate the anchor. The channel may extend along part or all of a length between the plurality of fenestrations and the tail anchor retaining section. The channel may be defined by one or more leash. The one or more leash may comprise two leashes defining the channel or one leash partly defining the channel. The two leashes may extend to either side of the anchor retaining section. The single leash may extend to one side of the anchor retaining section. When the one or more leash comprises a plurality of leashes, each leash may extend in parallel to the others. The one or more leash may be comprised as part of one or more spacer.

In one particular embodiment the one or more spacer; insert; and/or one or more leash may be more flexible than the fenestration section. The one or more spacer; insert; and/or the one or more leash may be long enough to fold back or partly fold to allow at least a part of an anchor to pass through a fenestration.

The one or more spacer; insert; and/or one or more leash may comprise a circular, ovoid, hexagonal or composite cross sectional profile, or may comprise a thread. The thread may comprise a suture thread.

Each hook or clasp may comprise a circular, ovoid, hexagonal, polygonal or composite cross-sectional profile.

The device may comprise a length of 5 to 35 cm; 10 to 25 cm; or 15 to 20 cm. The device length may comprise 5; 6;

7; 8; 9; 10; 11; 12; 13; 14; 15; 16; 17; 18; 19; 20; 21; 22; 23; 24; 25; 26; 27; 28; 29; 30; 31; 32; 33; 34; or 35 cm. In one particular embodiment, the device length comprises 17.0 cm. In another particular embodiment, the device length comprises 17.7 cm.

The lead anchor and/or tail anchors may comprise a length of 0.5 to 3.0 cm; 0.75 to 1.5 cm; or 0.80 to 1.25 cm. The lead anchor and/or tail anchors may comprise a length of 0.5; 0.6; 0.7; 0.8; 0.9; 1.0; 1.1; 1.2; 1.3; 1.4; 1.5; 1.6; 1.7; 1.8; 1.9; 2.0; 2.1; 2.2; 2.3; 2.4; 2.5; 2.6, 2.7; 2.8; 2.9 or 3.0 cm. In a particular embodiment, the lead anchor and/or tail anchor may comprise a length of 1.0 cm. In another particular embodiment, the lead anchor and/or tail anchor may comprise a length of 1.65 cm.

One or more of the anchor retaining sections may comprise a length of 0.5 to 2.5 cm; 1.0 to 2.0 cm; or 1.25 to 1.75 cm. The anchor retaining sections may comprise a length of 0.5; 0.6; 0.7; 0.8; 0.9; 1.0; 1.1; 1.2; 1.3; 1.4; 1.5; 1.6; 1.7; 1.8; 1.9; 2.0; 2.1; 2.2; 2.3; 2.4 or 2.5 cm. In a particular embodiment, the anchor retaining sections comprise a length of 1.5 cm. In another particular embodiment, the anchor retaining sections comprise a length of 1.55 cm.

The thickness of the insert may be approximately 0.5 to 3.5 mm; 0.75 to 3.25 mm; or 1.0 to 3.0 mm. The thickness of the insert may be 0.5; 0.6; 0.7; 0.8; 0.9; 1.0; 1.1; 1.2; 1.3; 1.4; 1.5; 1.6; 1.7; 1.8; 1.9; 2.0; 2.1; 2.2; 2.3; 2.4; 2.5; 2.6; 2.7; 2.8; 2.9; 3.0; 3.1; 3.2; 3.3; 3.4; or 3.5 mm. In one particular embodiment, the thickness of the insert is 1.2 mm. In another particular embodiment, the thickness of the insert is 2.4 mm.

The width of the insert may be approximately 1.0 to 8.0 mm; 1.5 to 7.5 mm or 1.75 to 7.5 mm. The width of the insert may be 1.0; 1.1; 1.2; 1.3; 1.4; 1.5; 1.6; 1.7; 1.8; 1.9; 2.0; 2.1; 2.2; 2.3; 2.4; 2.5; 2.6; 2.7; 2.8; 2.9; 3.0; 3.1; 3.2; 3.3; 3.4; 3.5; 3.6; 3.7; 3.8; 3.9; 4.0; 4.1; 4.2; 4.3; 4.4; 4.5; 4.6; 4.7; 4.8; 4.9; 5.0; 5.1; 5.2; 5.3; 5.4; 5.5; 5.6; 5.7; 5.8; 5.9; 6.0; 6.1; 6.2; 6.3; 6.4; 6.5; 6.6; 6.7; 6.8; 6.9; 7.0; 7.1; 7.2; 7.3; 7.4; 7.5; 7.6; 7.7; 7.8; 7.9; or 8.0 mm. In one particular embodiment, the width of the insert is 2.0 mm. In another particular embodiment, the width of the insert is 6.5 mm.

The fenestration section may comprise a width of 3.5 to 8.0 mm; 4.0 to 7.5 mm or 4.25 to 7.0 mm. The width may comprise 3.5; 3.6; 3.7; 3.75; 3.8; 3.9; 4.0; 4.1; 4.2; 4.25; 4.3; 4.4; 4.5; 4.6; 4.7; 4.75; 4.8; 4.9; 5.0; 5.1; 5.2; 5.3; 5.4; 5.5; 5.6; 5.7; 5.8; 5.9; 6.0; 6.1; 6.2; 6.3; 6.4; 6.5; 6.6; 6.7; 6.8; 6.9; 7.0; 7.1; 7.2; 7.3; 7.4; 7.5; 7.6; 7.7; 7.8; 7.9; or 8.0 mm. In a particular embodiment, the width of the fenestration section is 4.5 mm. In another particular embodiment, the width is 6.5 mm.

The distance from a lead end to a first fenestration may be 2.5 to 7.5 cm; 3.0 to 7.0 cm; or 4.0 to 6.0 cm. The distance from a lead end to a first fenestration may be 2.5; 2.6; 2.7; 2.8; 2.9; 3.0; 3.1; 3.2; 3.3; 3.4; 3.5; 3.6; 3.7; 3.8; 3.9; 4.0; 4.1; 4.2; 4.3; 4.4; 4.5; 4.6; 4.7; 4.8; 4.9; 5.0; 5.1; 5.2; 5.3; 5.4; 5.5; 5.6; 5.7; 5.8; 5.9 or 6.0 cm. In a particular embodiment, the distance from a lead end to a first fenestration is 4.5 cm.

The distance from a tail end to a final fenestration may be 3.0 to 7.0 cm; 3.5 to 6.5 cm; or 4.0 to 5.0 cm. The distance from a tail end to a final fenestration may be 3.0; 3.1; 3.2; 3.3; 3.4; 3.5; 3.6; 3.7; 3.8; 3.9; 4.0; 4.1; 4.2; 4.3; 4.4; 4.5; 4.6; 4.7; 4.8; 4.9; 5.0; 5.1; 5.2; 5.3; 5.4; 5.5; 5.6; 5.7; 5.8; 5.9; 6.0; 6.1; 6.2; 6.3; 6.4; 6.5; 6.6; 6.7; 6.8; 6.9; or 7.0 cm. In one particular embodiment, the distance from a tail end to a final fenestration is 4.5 cm. In another particular embodiment, the distance from a tail end to a final fenestration is 5.0 cm.

The width of the hooks may be approximately 0.4 to 1.5 mm.

The width of the hooks may be 0.4; 0.5; 0.6; 0.7; 0.8; 0.9; 1.0; 1.1; 1.2; 1.3; 1.4; or 1.5 mm. In a particular embodiment the width of the hooks is 1.2 mm.

The elongate body may comprise one or more wings. The one or more wing may be able to distribute force more evenly. The one or more wing may comprise a width of 10.0 to 25.0 mm; 10.0 to 20.0 mm or 10.0 to 15.0 mm; or greater than 25.0 mm. The width of the wider section may be 10.0; 11.0; 12.0; 13.0; 14.0; 15.0; 16.0; 17.0; 18.0; 19.0; 20.0; 21.0; 22.0; 23.0; 24.0; or 25.0 mm.

The one or more wing may be at any section along the elongate body length. The length of the one or more wing may be equivalent to or shorter than the length of the elongate body; the length of the fenestration section; or the length of the spacer. The length of the one or more wing may be 5.0 to 15.0 cm. The one or more wing length may comprise 5; 6; 7; 8; 9; 10; 11; 12; 13; 14; or 15 cm. In a particular embodiment, the one or more wing may comprise 10.0 cm.

The one or more wing thickness may comprise 1.0 to 3.0 mm; 1.5 to 2.5 mm or 1.75 to 2.25 mm. The one or more wing thickness may be 1.0; 1.1; 1.2; 1.3; 1.4; 1.5; 1.6; 1.7; 1.8; 1.9; 2.0; 2.1; 2.2; 2.3; 2.4; 2.5; 2.6; 2.7; 2.8; 2.9 or 3.0 mm. In a particular embodiment, the one or more wing thickness is 2.0 mm.

The one or more wing may comprise an equivalent length or differing lengths.

In another embodiment, the surgical device comprises one or more branch elongate body, each of the one or more branch elongate body comprising a plurality of fenestrations along a branch elongate body length wherein each fenestration is sized to receive at least part of one of the anchors. The branch elongate body may comprise a branch anchor at each end or at a branch end. The branch elongate body may extend from the elongate body and comprise an anchor at a branch end. The branch elongate body may extend from a spacer. The branch elongate body may comprise a stopper preventing a tail end of the branch elongate body being pulled through any of the plurality of fenestrations.

The branch elongate body may comprise the same features, shape and dimensions as the elongate body. The branch elongate body may comprise a lead end and/or a tail end.

Each branch anchor may comprise the same features, shape and dimensions as the lead anchor and/or the tail anchor.

The surgical device may comprise an X-shape; a Y-shape; a T-shape; an L-shape or an I-shape. The surgical device may comprise one, two, three, four, five, six, seven, eight, nine, ten, or more than ten branch elongate bodies.

The surgical device may further comprise one or more bridge spanning between two or more branch elongate bodies and/or the elongate body. The surgical device may comprise one, two, three, four, five, six, seven, eight, nine, ten, or more than bridges In a particular embodiment the device is dimensioned so that it can be retrieved through a 5 mm port. The device may also be cut at the end of use such that it may be removed in sections.

The elongate body, one or more branch elongate body and one or more bridge may be comprised of silicone, any biocompatible synthetic material or combination thereof.

The anchors may be comprised of silicone, metal, polycarbonate, any biocompatible synthetic material or combination thereof. In a preferred embodiment each of the hooks are comprised of stainless steel wire.

Another embodiment may comprise a tail anchor at each end, that is, both anchors may engage with fenestrations along the elongate body.

In a second aspect, the invention provides a method of manufacturing a surgical device for retraction of a body part, the method comprising:
  forming an elongate body comprising a plurality of fenestrations along a body length wherein each fenestration is sized to receive at least part of one of the anchors; and
  attaching an anchor to each end of the surgical device;
  wherein the surgical device comprises a stopper preventing the tail end of the device being pulled through any of the plurality of fenestrations.

The method may further comprise attaching one or more branch elongate body.

The method may further comprise attaching one or more bridge spanning between two or more branch elongate bodies and/or the elongate body.

The method for manufacturing the first embodiment of the device of the invention may be carried out by using techniques known in the field of silicone injection moulding and surgical needle and/or suture manufacture.

The surgical device manufactured according to the second aspect may comprise the surgical device of the first aspect.

In a third aspect of the invention, there is provided a method for inserting the first embodiment of the invention into an incision in a patient, the method comprising the steps of:
  inserting a surgical trocar into the incision;
  grasping one anchor and inserting it beyond a seal within the trocar, then feeding the elongate body of the device into the trocar, followed by the other anchor;
  inserting the lead anchor onto a first site;
  straightening out the body of the retractor against the organ to be retracted; and
  inserting the tail anchor through an appropriate fenestration along the elongate body, and thereon into the site of the second anchorage.

The invention also provides a kit comprising the device of the invention and a vacuum retractor. The device of the invention and the vacuum retractor provide complementary retraction.

Any discussion of the prior art throughout the specification should in no way be considered as an admission that such prior art is widely known or forms part of the common general knowledge in the field.

As used herein, except where the context requires otherwise, the term "comprise" and variations of the term, such as "comprising", "comprises" and "comprised", are not intended to exclude further additives, components, integers or steps.

BRIEF DESCRIPTION OF THE FIGURES

In order that the present invention may be readily understood and put into practical effect, reference will now be made to the accompanying illustrations, wherein like reference numerals refer to like features.

FIG. 7 is a schematic diagram showing a top perspective view of the embodiment shown in FIG. 1.

FIG. 8 is a schematic diagram showing a bottom top perspective view of the embodiment shown in FIG. 1.

FIG. 11A is a schematic diagram showing a surgical device comprising wings along the length of the fenestration section according to one embodiment of the invention.

FIG. 11B is a schematic diagram showing wings along part of the spacer according to one embodiment of the invention.

DETAILED DESCRIPTION OF THE INVENTION

Embodiments of the present invention relate to a surgical device for retraction of a body part.

The retractor of the invention varies the length between two anchor points in a novel manner, by having "fenestrations" or loops along part of the length of the span, through which one of the anchors can be inserted. The anchor which is inserted through a selected fenestration or window must have a stopper or stopping portion which prevents the window sliding over the anchor.

Figure 1:
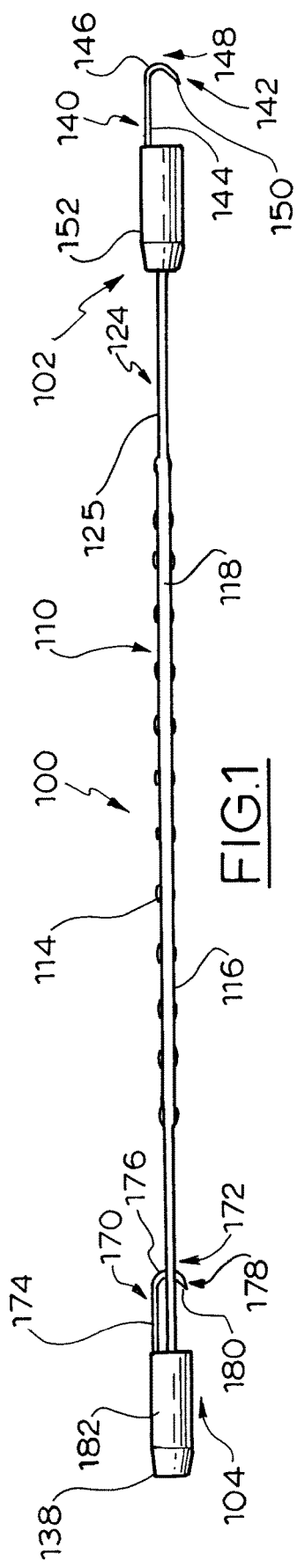
FIG. 1 is a schematic diagram showing a side view of one embodiment of a device according to the invention.

FIG. 1 shows one embodiment of a surgical device 100 for retraction of a body part according to the invention. The device 100 comprises an anchor 140, 170 at each end of the surgical device and an elongate body 110.

The elongate body 110 comprises a plurality of fenestrations 112 along the body length. To achieve the effect of an adjustable length, each fenestration 112 is sized to receive at least part of one of the anchors 140, 170.

The elongate body 110 comprises a head end 102 and a tail end 104 and comprises a strip shape or substantially a strip shape and comprises a top surface 114 and a bottom surface 116. The top 114 and bottom surfaces 116 may be flat or substantially flat. The elongate body 110 also comprises rounded edges 118 between the top 114 and bottom surfaces 116.

In other embodiments, the elongate body 110 comprises a round, ovoid or other shape. From the teaching herein, the skilled person is able to select other suitable shapes for elongate body 110. The elongate body 110 may be substantially planar in cross-sectional profile.

Figure 13:
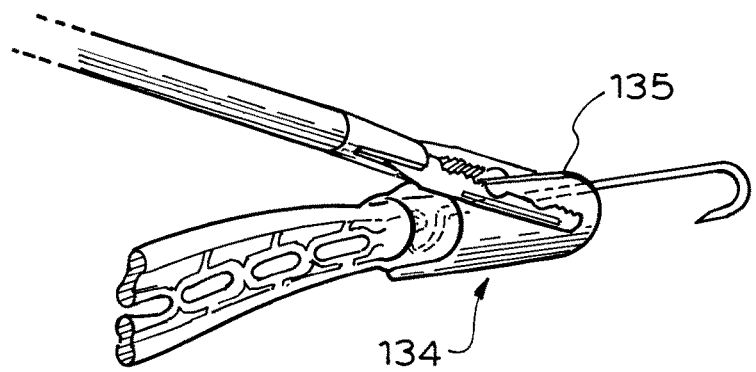
FIG. 13 is a schematic diagram showing the anchor retaining section being grasped by a laparoscopic grasper.
Figure 15:
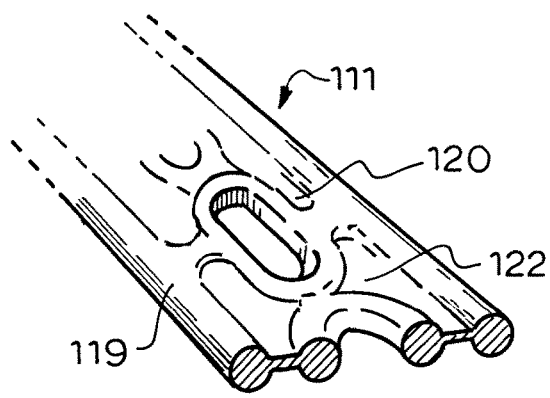
FIG. 15 is a schematic diagram showing thickened side rims and reinforcement according to one embodiment of the invention.

FIGS. 13 and 15 show an embodiment in which elongate body 110 comprises side rims 119. The side rims 119 have an increased thickness compared to the remainder of elongate body 110. The side rims 119 comprise a thickness of 2.0 to 3.0 mm; 2.2 to 2.6 mm; or 2.3 to 2.5 mm. The thickness may comprise 2.0; 2.1; 2.2; 2.3; 2.4; 2.5; 2.6; 2.7; 2.8; 2.9 or 3.0 mm. In the embodiment shown in FIGS. 13 and 15, the thickness of side rims 119 is 2.4 mm.

The elongate body 110 may comprise a width of 2.0 to 50.0 mm; 4.0 to 25.0 mm or 5.0 to 20.0 mm. The width may comprise 2.0; 2.5; 3.0; 3.5; 4.0; 4.5; 5.0; 5.1; 5.2; 5.3; 5.4; 5.5; 5.6; 5.7; 5.8; 5.9; 6.0; 6.1; 6.2; 6.3; 6.4; 6.5; 6.6; 6.7; 6.8; 6.9; 7.0; 7.1; 7.2; 7.3; 7.4; 7.5; 7.6; 7.7; 7.8; 7.9; 8.0; 8.1; 8.2; 8.3; 8.4; 8.5; 8.6; 8.7; 8.8; 8.9; 9.0; 9.1; 9.2; 9.3; 9.4; 9.5; 9.6; 9.7; 9.8, 9.9; 10.0; 10.1; 10.2; 10.3; 10.4; 10.5; 10.6 10.7; 10.8; 10.9; 11.0; 11.1; 11.2; 11.3; 11.4; 11.5; 11.6; 11.7; 11.8; 11.9; 12.0; 12.1; 12.2; 12.3; 12.4; 12.5; 12.6; 12.7; 12.8, 12.9; 13.0; 13.1; 13.2; 13.3; 13.4; 13.5; 13.6; 13.7; 13.8; 13.9; 14.0; 14.1; 14.2; 14.3; 14.4; 14.5; 14.6; 14.7; 14.8; 14.9; 15.0; 15.5; 16.0; 16.5; 17.0; 17.5; 18.0; 18.5; 19.0; 19.5; 20.0; 20.5; 21.0; 21.5; 22.0; 22.5; 23.0; 23.5; 24.0; 24.5; 25.0; 25.5; 26.0; 26.5; 27.0; 27.5; 28.0 28.5; 29.0; 29.5; 30.0 30.5; 31.0; 32.0; 33.0; 34.0; 35.0; 36.0; 37.0; 38.0; 39.0; 40.0; 41.0; 42.0; 43.0; 44.0; 45.0; 46.0; 47.0; 48.0; 49.0; or 50.0 mm. In the embodiment shown in FIGS. 1 and 2 the width is 4.5 mm, while in the embodiment shown in FIGS. 13 to 18 the width is 6.5 mm.

Although the elongate body 110 is shown to have a smooth surface, in other embodiments, the elongate body 110 may comprise one or more textured or partially textured surface. The textured or partially textured surface may be comprised on part or all of the elongate body 110 or one or more part thereof such as, fenestration section 111; spacer 124; insert; 125; one or more leash 126; or anchor retaining section 134. Advantageously, the textured surface or partially textured surface may be provided to increase friction.

The plurality of fenestrations 112 are arranged in series along the body length in fenestration section 111 of elongate body 110. Each of the plurality of fenestrations 112 may comprise an elongate shape. Although the plurality of fenestrations 112 are shown to comprise an oval shape, other shapes may be used, such as a rectangular shape. The shape need not be elongate, only large enough for part of one of the anchors 140, 170 to pass through it as a minimum.

Importantly, each fenestration 112 is large enough receive at least part of one of the anchors 140, 170.

Figure 6:
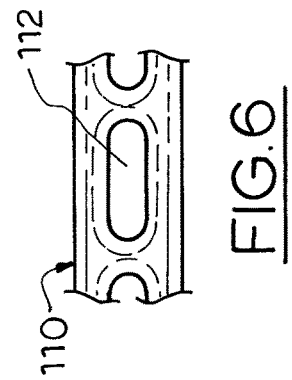
FIG. 6 is a detailed view of region VI shown in FIG. 2.

Each of the plurality of fenestrations 112 are defined or partly defined by a reinforcement 120. The reinforcement 120 may comprise a bordering section of thickened material. As shown in FIG. 6, neighbouring reinforcements 120 may abut each other. FIG. 15 shows another embodiment in which neighbouring reinforcements 120 are continuous with one another.

The reinforcement 120 may have the same thickness as the side rims 119 and may comprise a thickness of 2.0 to 4.0 mm; 2.2 to 3.0 mm; or 2.3 to 2.5 mm. The thickness may comprise 2.0; 2.1; 2.2; 2.3; 2.4; 2.5; 2.6; 2.7; 2.8; 2.9; 3.0; 3.1; 3.2; 3.3; 3.4; 3.5; 3.6; 3.7; 3.8; 3.9 or 4.0 mm. In the embodiment shown in FIG. 1 the thickness is 2.4 mm.

Although not shown, one or more of the plurality of fenestrations 112 may be membranous, such that the fenestration membrane 113 (not shown) covering the fenestration 112 can be penetrated by one or each of the anchors 140, 170.

In other embodiments, the elongate body 110 may comprise one or more wall 122 between neighbouring fenestrations 112. The wall 122 may be thinner than the reinforcement 120. The wall 122 may comprise a thickness of 0.5 to 5.0 mm; 0.7 to 4.0 mm; or 0.8 to 3.0 mm. The thickness may comprise 0.5; 0.6; 0.7; 0.8; 0.9; 1.0; 1.1; 1.2; 1.3; 1.4; 1.5; 1.6; 1.7; 1.8; 1.9; 2.0; 2.1; 2.2; 2.3; 2.4; 2.5; 2.6, 2.7; 2.8; 2.9; 3.0; 3.1; 3.2; 3.3; 3.4; 3.5; 3.6; 3.7; 3.8; 3.9; 4.0; 4.1; 4.2; 4.3; 4.4; 4.5; 4.6; 4.7; 4.8; 4.9; or 5.0 mm. In the embodiment shown in FIGS. 13 and 15, the thickness of wall 122 is 1.0 mm. In the embodiment shown in FIGS. 17 and 18, the thickness of wall 122 is 2.4 mm.

Figure 2:
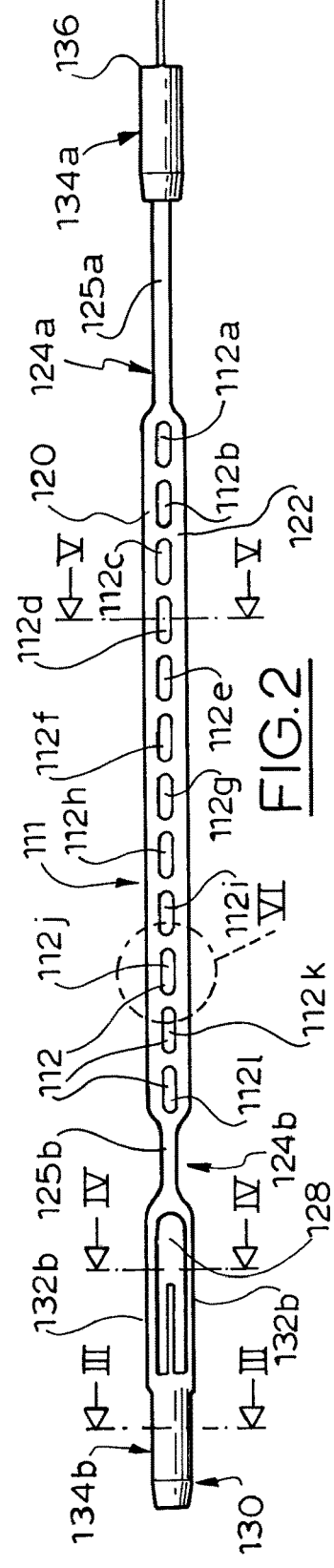
FIG. 2 is a schematic diagram showing a top view of the embodiment shown in FIG. 1.

FIGS. 1 and 2 show the elongate body 110 to comprise twelve fenestrations 112a,b,c,d,e,f,g,h,i,j,k,l. From the teachings herein a skilled person is readily able to select other suitable number of fenestrations.

In a particular embodiment, the elongate body 110 is sufficiently flexible to fold back or partly fold back on itself. The elongate body 110 is sufficiently flexible or substantially flexible so that it can be bent or folded to allow at least a part of tail anchor 170 to pass through a fenestration 112 to allow the anchor 170 to attach to tissue. The selection of which fenestration 112a,b,c,d,e,f,g,h,i,j,k,l to penetrate allows the length of device 100 to be customised. That is, if tail anchor 170 is passed through fenestration 112a, the device 100 anchored at both or each anchor 140 and tail anchor 170, will have a shorter length than if tail anchor were to be passed through fenestration 112b, or any other fenestration 112c,d, e,f,g,h,i,j,k,l.

FIG. 1 shows the elongate body 110 to comprise a spacer 124 between the plurality of fenestrations and each of the lead anchor 140 and the tail anchor 170. In other embodiments, the elongate body 110 may comprise a spacer 124b between only the plurality of fenestrations 112 and the tail anchor 170, a spacer 124a between only the plurality of fenestrations 112 and the lead anchor 140, or no spacer 124. When there is no spacer 124, the fenestration section 111 connects directly to the anchor 140, 170.

In FIG. 1, lead spacer 124a is comprised solely of insert 125a, while tail spacer 124b comprises both insert 125b and leashes 132b.

In FIG. 1, leashes 132b are shown to comprise a circular cross-section profile, while insert 125 comprises a thread shape. In other embodiments, spacer 124 may comprise an ovoid, hexagonal, polygonal or composite cross-sectional profile. From the teaching herein, a skilled person is readily able to select a suitable cross-sectional profile shape for inserts 124 and one or more leashes 132.

Lead spacer 124a is shown in FIG. 1 to be a solid unitary length comprising an insert 125. Tail spacer 124b comprises both insert 125b and one or more leash 132b defining one or more orifice or channel 128. From the teaching herein a skilled person is readily able to select other suitable forms for spacers 124.

The channel 128 may accommodate the tail anchor 170. The channel 128 may extend along part or all of a length between the plurality of fenestrations 112 and the tail anchor retaining section 134b. The channel 128 may be defined by one or more leash 132. In the embodiment shown in FIG. 2, channel 128 is defined by two leashes 132b. In the embodiment shown in FIG. 17, channel 128 is partly defined by a single leash 132 extending on one side. The leashes 132 may extend to either side of the anchor retaining section 134a,b. When only a single leash 132 is present, single leash 132 extends to one side of the anchor retaining section 134 a,b.

Like spacer 124, insert 125 and one or more leash 132 may have any suitable cross-sectional profile shape, such as, circular, ovoid, hexagonal, polygonal or composite. The spacer 124; insert 125 and one or more leash 132 may comprise a thread such as a surgical thread.

As shown in FIGS. 1, 2 and 17 and 18, channel 128 accommodates tail hook 172. In other embodiments, channel 128 may accommodate a clasp or other component of anchor 140, 170.

In the embodiment shown in FIGS. 1 and 2 tail spacer 124 comprises two separate leashes 132b. The separate leashes 132b extend in parallel and attach to different sides of tail anchor retaining section 134b like a swing.

In one embodiment, the one or more spacer 124; insert 125; and or one or more leash 132 may be more flexible than the fenestration section 111. The one or more spacer 124; insert 125; and/or one or more leash 132 may be long enough to fold back or partly fold to allow at least a part of an anchor 140, 170 to pass through a fenestration 112. This embodiment may advantageously provide a less flexible elongate body 110 that is better able to provide an increased level of support for retraction. The one or more spacer 124; insert 125; and/or one or more leash 132 may provide a line providing freedom of movement of the tail anchor.

Although not shown, elongate body 110 may also comprise one or more linker 126 (not shown) to attach to one or both of anchors 140,170. Linkers 126 may comprise a clip or other suitable connection or fastener. From the description herein, a skilled person is readily able to select other suitable linkers 126.

The elongate body 110 also comprises anchor retaining sections 134. The anchor retaining sections 134 comprise a head end anchor retaining section 134a and a tail end anchor retaining section 134b. Each of the anchor retaining sections 134a,134b comprise an appropriate thickness for the anchors 140, 170 to be inserted therein. The anchors 140, 170 may be inserted in parallel with the elongate body 110, at an angle or offset from parallel. The anchor retaining sections 134a,134b may comprise a one-way attachment for receiving the anchor 140,170.

Figure 16:
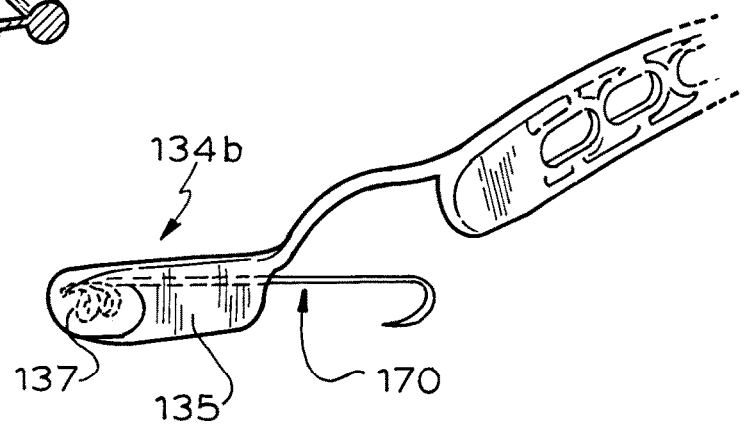
FIG. 16 shows a single leash according to another embodiment of the invention.

In the embodiment shown in FIGS. 13 and 16, anchor retaining sections 134 comprise a thin flat segment 135 and a thicker base 137. The thin flat segment 135 may be suitable for grasping. The thicker base 137 may be suitable for retaining an anchor.

Figure 5:
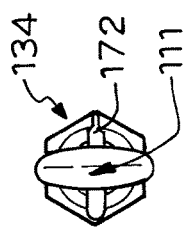
FIG. 5 is a cross-sectional view along section V-V shown in FIG. 2.
Figure 4:
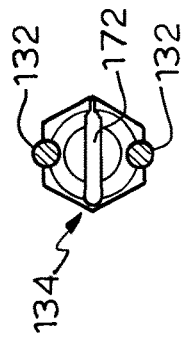
FIG. 4 is a cross-sectional view along section IV-IV shown in FIG. 2.
Figure 3:
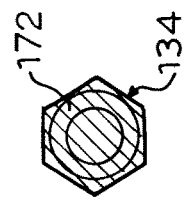
FIG. 3 is a cross-sectional view along section shown in FIG. 2.

As shown in FIGS. 3, 4 and 5, different components of the elongate body 110 may comprise different profiles. As shown in FIG. 3, the anchor retaining section 134 comprises a hexagonal profile and the width is 4.3 mm across the flat and 4.9 mm across the points. As shown in FIG. 4, the leashes 132 comprise a circular or ovoid profile and each leash 132 comprises a width of 1.0 mm and a thickness of 1.1 mm. As shown in FIG. 5 the fenestration section 111 comprises an ovoid profile and has a width of 1.6 min. In other embodiments the fenestration section 111 may comprise a hexagonal profile.

FIG. 6 shows a detailed view of part of fenestration section 11 including one fenestration 112. Each fenestration 112a-1 has a length of 5.0 mm and a width of 1.5 mm. Based on the teaching herein a skilled person is readily able to select other suitable sizes for fenestrations 112 and anchors 140, 170.

Figure 14:
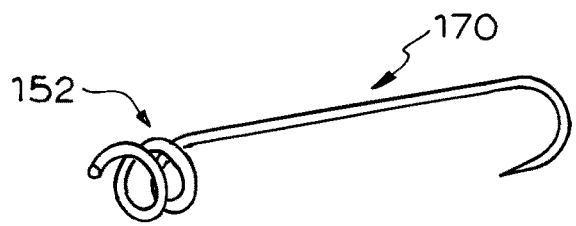
FIG. 14 is a schematic diagram showing a coiled retainer according to one embodiment of the invention.

The anchors 140, 170 may be a simple design. As shown in FIGS. 1 and 2, the anchors 140, 170 may be attached to the elongate body 110 directly by being inserted into the material of the anchor retaining section 134a,134b to retain anchors 140, 170 within the device 100. The anchors 140, 170 comprise one or more retainers 152, 182 which engage with elongate body 110. FIGS. 13, 14 and 16 show retainers 152, 182 to comprise coils that are wound or moulded into elongate body 110. In other embodiments retainers 152, 182 may comprise one or more retention barbs (see FIGS. 9A and B).

Each anchor 140, 170 may comprise or consist of a hook 142, 172. The hooks 142, 172 may comprise an elongate segment 144,174; a curved segment 146,176; a point segment 148,178; and a point 150,180. The elongate sections 144, 174 may comprise one or more stopper 130 comprising branches or protrusions 154,184 (see FIG. 9). The one or more stopper branches or protrusions 154,184 may extend from the elongate segment 144, 174.

The elongate segment 144,174 may be linear or may comprise one or more bends 145, 175. The bends 145,175, when present, assist in orienting the anchor 140,170 for ease of placement. The curved segment 146, 176 may comprise a 180° turn so the point extends parallel to the elongate segment.

In the embodiment shown in FIGS. 13, 16, 17 and 18, hooks 142, 172 curve in the plane of the elongate body 110. This is advantageous because it keeps hooks 142, 172 flat in packaging and renders perforation less likely. In other embodiments, hooks 142, 172 curve at an angle to the elongate body 110. For example, in the embodiment shown in FIGS. 1 and 2 hooks 142, 172 curve perpendicularly to the plane of elongate body 110.

In another embodiment, one or both of the anchors 140, 170 may comprise a complementary one-way attachment (not shown) to be received in the anchor retaining section one-way attachment (not shown). The one-way attachment and complementary one-way attachment may comprise male and female attachments.

The anchors 140, 170 may be comprised of silicone, metal or polycarbonate. In the embodiment shown in the Figures the anchors 140, 170 are comprised of stainless steel wire.

As is apparent from above, the stopper 130 which prevents the tail end 104 from being pulled through any of the plurality of fenestrations 112 may comprise a region of the elongate body 110 larger than the width of the fenestration 112 such as, anchor retaining section 134a,b in the embodiment shown in FIG. 1. In the embodiment shown in FIGS. 17 and 18, stopper 130 comprises a branch or protrusion 131 extending from anchor retaining section 134a, 134b.

Figures 9A, 9B:
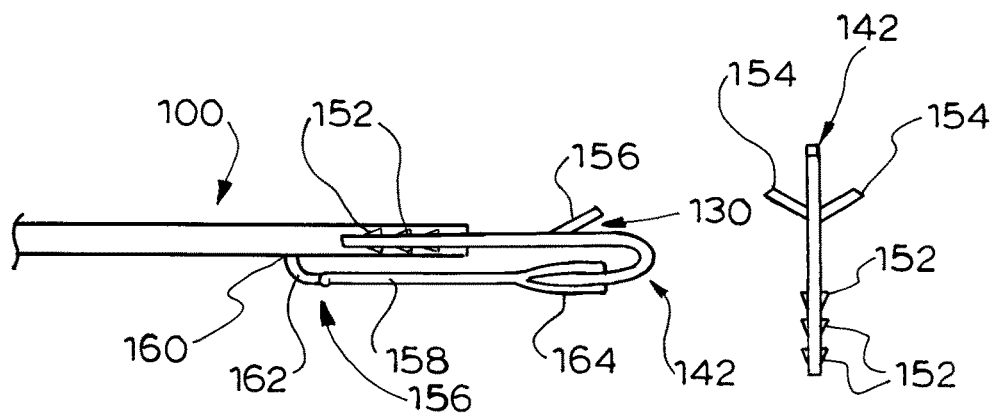
FIG. 9A is a schematic diagram showing another embodiment of the invention.
FIG. 9B is a schematic diagram showing the lead anchor according to the embodiment shown in FIG. 9A.

In the embodiment shown in FIGS. 9A and 9B, the stopper 130 comprises one or more branches or protrusions 154 comprised on one or each of the anchors 140, 170. The one or more branches or protrusions 154 may extend from the elongate segment 144, 174 of the hook 140,170. The elongate segment 144,174 may be linear or may comprise one or more bend.

The stopper 130 may be comprised on one or both anchors 140, 170 or at one or both ends 136, 138 of elongate body 110. In other embodiments, stopper 130 may only be comprised on a lead anchor 140 or a tail anchor 170 or at only one of end 136, 138.

The at least a part of one of the anchors received in the fenestration 112 may comprise the point segment 148, 178 to allow the anchoring.

The anchor points 150,180 may extend at any angle. Anchor points 150,180 may be flat against, perpendicular, substantially perpendicular, extend obliquely or extend at an angle to the elongate segment 144,174 of the tail hook 172 or to the elongate body 110.

FIG. 9A, shows an embodiment in which lead 170 anchor comprises a guard 156. The guard 156 comprises a stem 158, an attachment point 160, a bend 162 and a cap 164. In other embodiments, anchors 140, 170 may be identical, with or without a guard 156.

Figure 10A:
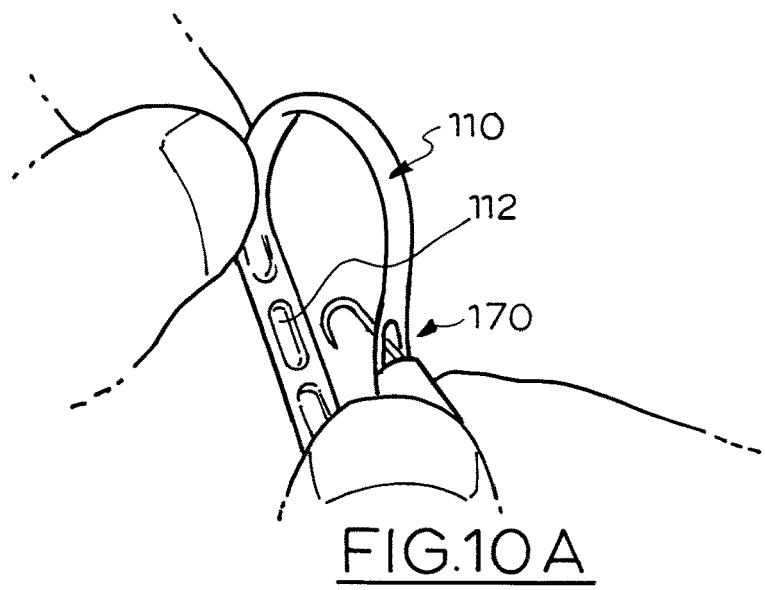
FIGS. 10A and 10B show an embodiment of the invention in use.
Figure 10B:
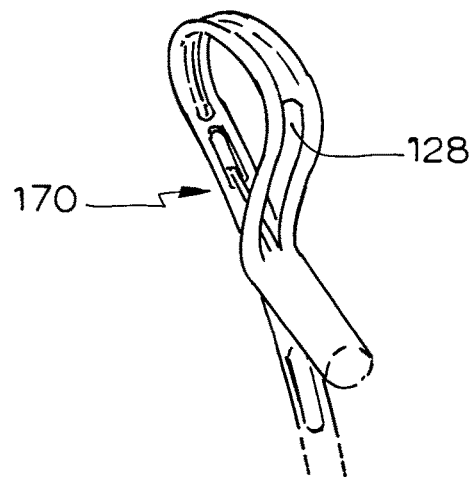

In the embodiment shown in FIG. 1, the lead anchor 140 and tail anchor 170 are oriented in the same direction. This orientation can also be clearly seen in the perspective top and bottom views of FIGS. 7 and 8. As shown in FIGS. 10A and 10B when the elongate body 110 is folded, so that tail anchor 170 can pass through a fenestration 112, this orientation of anchors 140,170 is most suitable for deployment.

The embodiment shown in FIG. 1, also shows elongate body 110 to comprise a channel 128 to accommodate the tail hook 172. The channel 128 may extend along part or all of a length between the end of the plurality of fenestrations 112 and the tail anchor 170.

Although the invention has been described with reference to hooks 142, in other embodiments the anchors may comprise one or more of a tissue clasp, a suture needle, a "T" bar, a surgical grasper, a barbed needle, a clasp or a rivet assembly.

The device 100 may comprise a length of 5 to 35 cm; 10 to 25 cm; or 15 to 20 cm. The device 100 length may comprise 5; 6; 7; 8; 9; 10; 11; 12; 13; 14; 15; 16; 17; 18; 19; 20; 21; 22; 23; 24; 25; 26; 27; 28; 29; 30; 31; 32; 33; 34 or 35 cm. In the embodiment shown in FIG. 1, the device 100 length comprises 17 cm. In the embodiment shown in FIG. 17, the device 100 length comprises 17.7 cm.

The lead anchor 140 and/or tail anchors 170 may comprise a length of 0.5 to 3.0 cm; 0.75 to 1.5 cm; or 0.80 to 1.25 cm. The lead anchor 140 and/or tail anchors 170 may comprise a length of 0.5; 0.6; 0.7; 0.8; 0.9; 1.0; 1.1; 1.2; 1.3; 1.4; 1.5; 1.6; 1.7; 1.8; 1.9; 2.0; 2.1; 2.2; 2.3; 2.4; 2.5; 2.6, 2.7; 2.8; 2.9 or 3.0 cm. In the embodiment shown in FIG. 1 the lead anchor 140 and/or tail anchor 170 comprise a length of 1.0 cm.

One or both of the anchor retaining sections 134a,b may comprise a length of 0.5 to 2.5 cm; 1.0 to 2.0 cm; or 1.25 to 1.75 cm. The lead and/or tail anchor retaining sections 134a,b may comprise a length of 0.5; 0.6; 0.7; 0.8; 0.9; 1.0; 1.1; 1.2; 1.3; 1.4; 1.5; 1.6; 1.7; 1.8; 1.9; 2.0; 2.1; 2.2; 2.3; 2.4 or 2.5 cm. In the embodiment shown in FIG. 1 anchor retaining sections may comprise a length of 1.5 cm. In the embodiment shown in FIG. 17, the anchor retaining sections comprise a length of 1.55 cm.

The thickness of the insert 125 may be approximately 0.5 to 3.5 mm; 0.75 to 3.25 mm; or 1.0 to 3.0 mm. The thickness of the insert 125 may be 0.5; 0.6; 0.7; 0.8; 0.9; 1.0; 1.1; 1.2; 1.3; 1.4; 1.5; 1.6; 1.7; 1.8; 1.9; 2.0; 2.1; 2.2; 2.3; 2.4; 2.5; 2.6; 2.7; 2.8; 2.9; 3.0; 3.1; 3.2; 3.3; 3.4; or 3.5 min. In the embodiment shown in FIG. 1, the thickness of the insert 125 is 1.2 mm. In the embodiment shown in FIG. 17, the thickness of the insert 125 is 2.4 mm.

The width of the insert 125 may be approximately 1.0 to 8.0 mm; 1.5 to 7.5 mm or 1.75 to 7.5 mm. The width of the insert 125 may be 1.0; 1.1; 1.2; 1.3; 1.4; 1.5; 1.6; 1.7; 1.8; 1.9; 2.0; 2.1; 2.2; 2.3; 2.4; 2.5; 2.6; 2.7; 2.8; 2.9; 3.0; 3.1; 3.2; 3.3; 3.4; 3.5; 3.6; 3.7; 3.8; 3.9; 4.0; 4.1; 4.2; 4.3; 4.4; 4.5; 4.6; 4.7; 4.8; 4.9; 5.0; 5.1; 5.2; 5.3; 5.4; 5.5; 5.6; 5.7; 5.8; 5.9; 6.0; 6.1; 6.2; 6.3; 6.4; 6.5; 6.6; 6.7; 6.8; 6.9; 7.0; 7.1; 7.2; 7.3; 7.4; 7.5; 7.6; 7.7; 7.8; 7.9; or 8.0 mm. In the embodiment shown in FIG. 1, the width of the insert 125 is 2.0 mm. In the embodiment shown in FIG. 17, the width of the insert 125 is 6.5 mm.

The fenestration section 111 may comprise a width of 3.5 to 8.0 mm; 4.0 to 7.5 mm or 4.25 to 7.00 mm. The fenestration section 111 may comprise a width of 3.5; 3.6; 3.7; 3.75; 3.8; 3.9; 4.0; 4.1; 4.2; 4.25; 4.3; 4.4; 4.5; 4.6; 4.7; 4.75; 4.8; 4.9; 5.0; 5.1; 5.2; 5.3; 5.4; 5.5; 5.6; 5.7; 5.8; 5.9; 6.0; 6.1; 6.2; 6.3; 6.4; 6.5; 6.6; 6.7; 6.8; 6.9; 7.0; 7.1; 7.2; 7.3; 7.4; 7.5; 7.6; 7.7; 7.8; 7.9; or 8.0 mm. In the embodiments shown in FIGS. 1 and 2 the width of the fenestration section 111 is 4.5 mm. In the embodiment shown in FIGS. 17 and 18 the width is 6.5 mm.

The distance from a lead end 136 to a first fenestration 112a may be 2.5 to 7.5 cm; 3.0 to 7.0 cm; or 4.0 to 6.0 cm. The distance from a lead end 136 to a first fenestration 112a may be 2.5; 2.6; 2.7; 2.8; 2.9; 3.0; 3.1; 3.2; 3.3; 3.4; 3.5; 3.6; 3.7; 3.8; 3.9; 4.0; 4.1; 4.2; 4.3; 4.4; 4.5; 4.6; 4.7; 4.8; 4.9; 5.0; 5.1; 5.2; 5.3; 5.4; 5.5; 5.6; 5.7; 5.8; 5.9 or 6.0 cm. In the embodiments shown in FIGS. 1 and 2 the distance from a lead end 126 to a first fenestration 112a is 4.5 mm.

The distance from a tail end 138 to a final fenestration 112l may be 3.0 to 7.0 cm; 3.5 to 6.5 cm; or 4.0 to 5.0 cm. The distance from a tail end 138 to a final fenestration 112l may be 3.0; 3.1; 3.2; 3.3; 3.4; 3.5; 3.6; 3.7; 3.8; 3.9; 4.0; 4.1; 4.2; 4.3; 4.4; 4.5; 4.6; 4.7; 4.8; 4.9; 5.0; 5.1; 5.2; 5.3; 5.4; 5.5; 5.6; 5.7; 5.8; 5.9; 6.0; 6.1; 6.2; 6.3; 6.4; 6.5; 6.6; 6.7; 6.8; 6.9; or 7.0 cm. In the embodiment shown in FIG. 1 the distance from a tail end 138 to a final fenestration 112l is 4.5 mm. In the embodiment shown in FIG. 17 the distance is 5.0 cm.

The width of the hooks 142, 172 may be approximately 0.4 to 1.5 mm. The width of the hooks 142, 172 may be 0.4; 0.5; 0.6; 0.7; 0.8; 0.9; 1.0; 1.1; 1.2; 1.3; 1.4; or 1.5 mm. In a particular embodiment the width of the hooks 142, 172 is less than 0.7 mm.

The elongate body 110 may comprise one or more wing 190. The one or more wing 190 may be able to distribute force more evenly. The one or more wing 190 may comprise a length of 5.0 to 15.0 cm. The one or more wing length may comprise 5; 6; 7; 8; 9; 10; 11; 12; 13; 14; or 15 cm.

The one or more wing thickness may comprise 1.0 to 3.0; 1.5 to 2.5 mm; or 1.75 to 2.25 mm. The one or more wing thickness may be 1.0; 1.1; 1.2; 1.3; 1.4; 1.5; 1.6; 1.7; 1.8; 1.9; 2.0; 2.1; 2.2; 2.3; 2.4; 2.5; 2.6; 2.7; 2.8; 2.9 or 3.0 min. In a particular embodiment, the one or more wing thickness is 2.0 mm.

From the teaching herein, the size of the one or more wing 190 can be selected by a skilled person according to the intended organ size to be retracted. A range of sizes may be offered for the surgeon to choose from. The one or more wing 190 may serve to distribute pressure over a wider area and therefore are positioned along the section of the elongate body 110 being applied against the organ retracted.

The one or more wing 190 may comprise an equivalent length or differing lengths.

FIGS. 11A and 11B shown device 100 to comprise bilateral wings 190. In the embodiment shown in FIG. 11A, bilateral wings 190 extend on either side of elongate body 110 and traverse the full length of the fenestration section 111. In FIG. 11B, bilateral wings 190 extend only part of the length of the one or more spacer 124.

Wings 190 may be at any section along the elongate body 110 length. The length of the one or more wing 190 may be equivalent to or shorter than the length of the elongate body 110; the length of the fenestration section 111; or the length of the one or more spacer 124.

In the embodiment shown in FIGS. 11A and 11B, the bilateral wings 190 comprise an equivalent length. In other embodiments, the wings 190 may be of differing lengths.

These wings 190 effectively represent variable widths of the elongate body 110.

While the wings 190 are, like elongate body 110, sufficiently flexible to fold back or partly fold back on themselves, they provide an increased surface area to better distribute force.

Figure 12A:
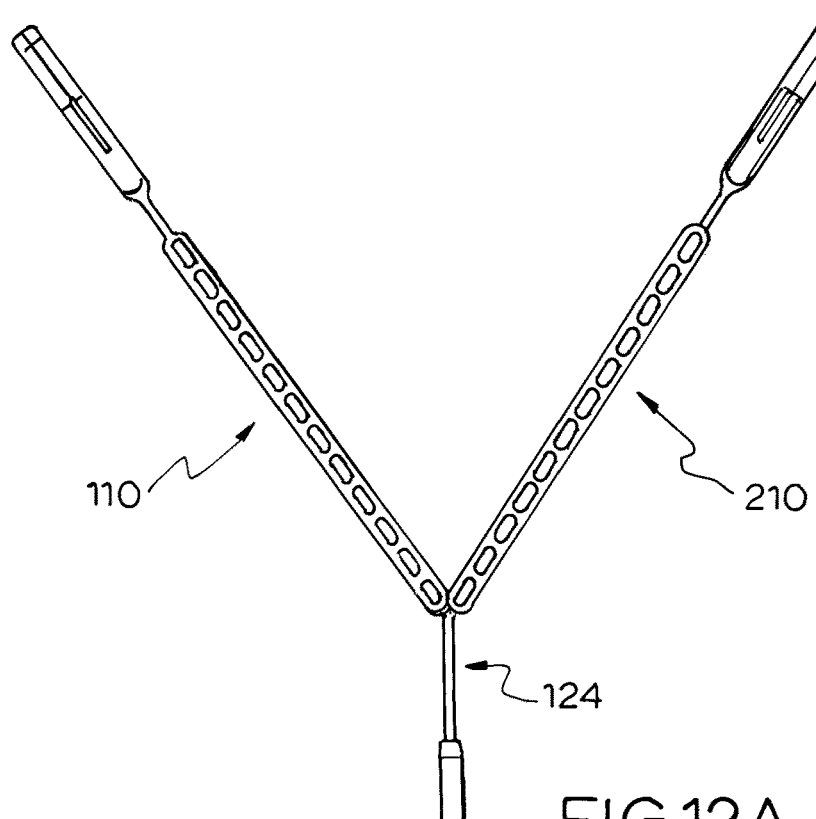
FIG. 12A is a schematic diagram showing a Y shaped surgical device according to one embodiment of the invention comprising one branch elongate body.
Figure 12B:
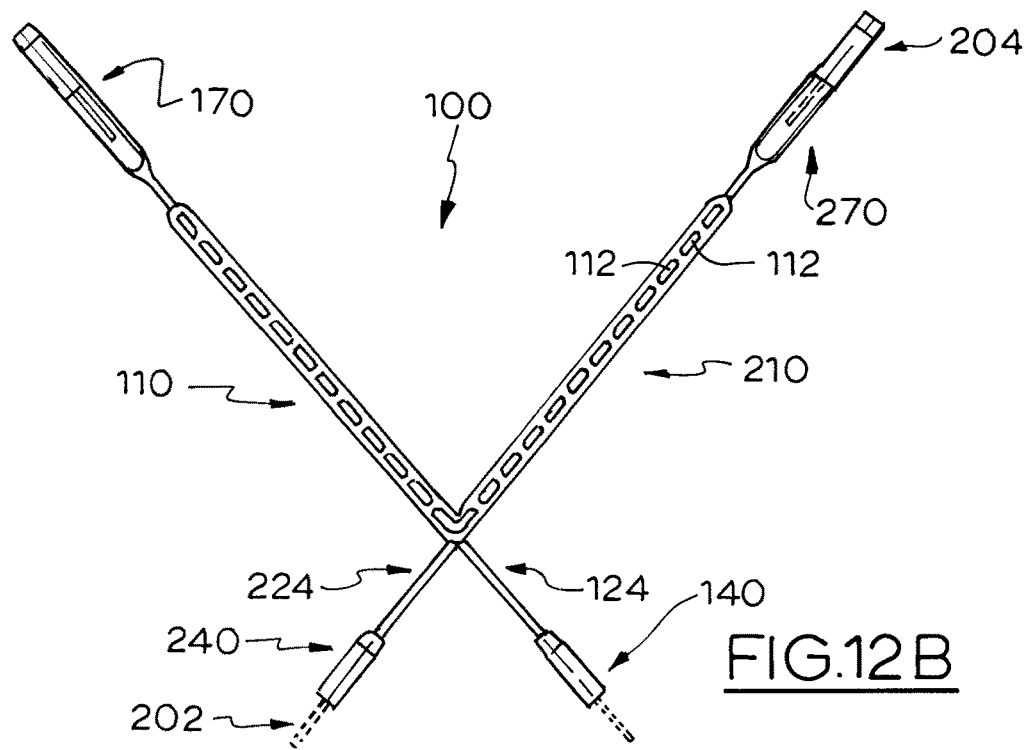
FIG. 12B is a schematic diagram showing an X shaped embodiment according to one embodiment of the invention comprising two branch elongate bodies.
Figure 12:
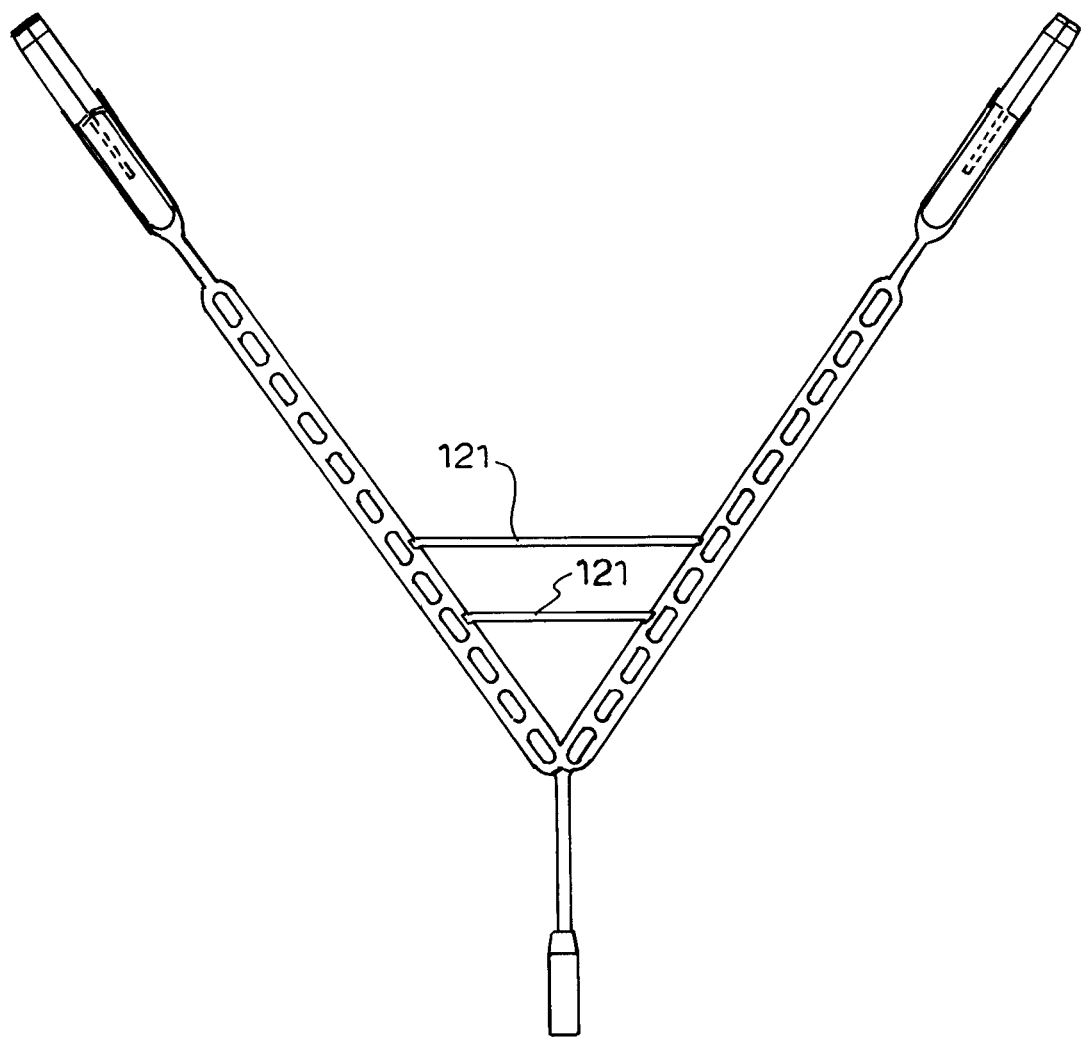
FIG. 12C is a schematic diagram showing a Y shaped surgical device incorporating two bridges according to one embodiment of the invention comprising one branch elongate body.
FIG. 12D is a schematic diagram showing a Y shaped surgical device comprising wings.

FIGS. 12A and 12B show embodiments of surgical device 100 comprising one or more branch elongate body 210. FIG. 12A shows a Y-shaped embodiment in which a single branch elongate body 210 extends from spacer 124. FIG. 12B shows an X-shaped embodiment in which a single branch elongate body 210, comprising branch lead anchor 240 and branch tail anchor 270, is joined to the elongate body 110 at their spacers 124, 224.

The branch elongate body 210 may comprise the same features, shape and dimensions as the elongate body 110. The branch elongate body 210 may comprise a branch head end 202 and a branch tail end 204.

Each of the one or more branch elongate body 210 may comprise a plurality of fenestrations 112 along a branch elongate body 210 length wherein each fenestration 112 is sized to receive at least part of one of the anchors 140, 170, 240, 270. The branch elongate body 210 may comprise a branch anchor 240, 270 at each branch end 202, 204. The branch elongate body 210 may extend from the elongate body 110 and comprise a branch anchor 240, 270 at a branch end 202, 204. The branch elongate body 210 may extend from a spacer 124, 224. The branch elongate body 210 may comprise a stopper 230 (not shown) preventing a tail end 238 of the branch elongate body 210 being pulled through any of the plurality of fenestrations 211.

Each branch anchor 240, 270 may comprise the same features, shape and dimensions as the lead anchor 140 and/or the tail anchor 170.

As well as the illustrated X- and Y-shapes the surgical device 100 may comprise a T-shape; an L-shape or an I-shape. The surgical device 100 may comprise one, two, three, four, five, six, seven, eight, nine, ten, or more than ten branch elongate bodies 210. From the teaching herein, a skilled person will recognise that the larger embodiments will not fit through a 5 mm port and will require insertion and removal through a larger port.

FIG. 12C shows an embodiment of surgical device 100 comprising two bridges 121 spanning between branch elongate body 210 and elongate body 110. One or more bridge 210 may also span between two branch elongate bodies 210. The surgical device 110 may comprise one, two, three, four, five, six, seven, eight, nine, ten, or more than bridges 121.

Figure 12D:
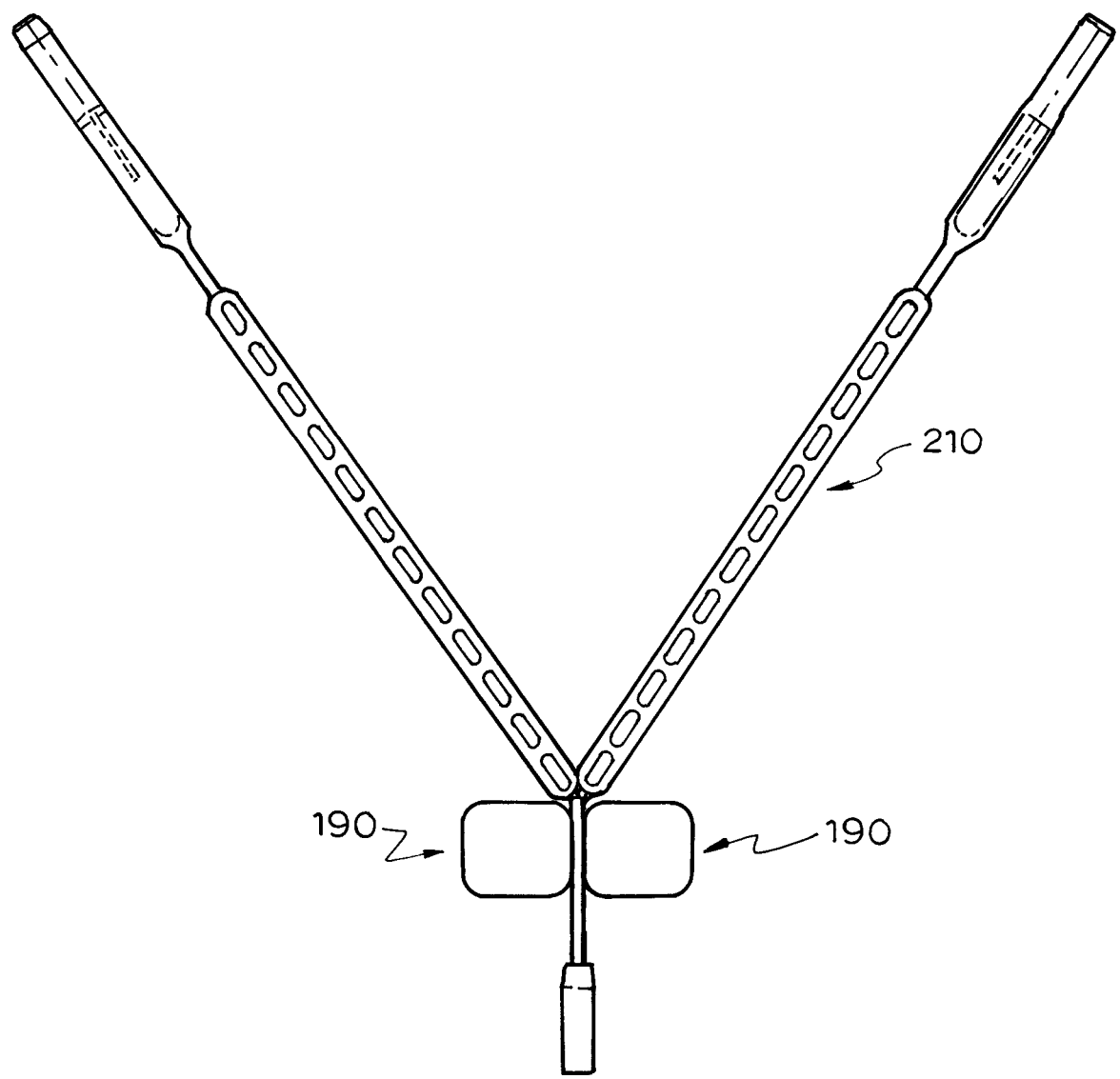

FIG. 12D shows an embodiment of surgical device 100 comprising both bilateral wings 190 and a branch elongate body 210.

In a particular embodiment the device 100 is dimensioned so that is can be retrieved through a 5 mm port. Advantageously, device 100 may be cut at the end of use such that it may be removed in sections.

The elongate body 110, one or more branch elongate body 210, bridges 121 and anchors 140, 170 may be comprised of silicone, any biocompatible synthetic material or combination thereof. The elongate body may be injection moulded.

The anchors 140, 170 may also be comprised of metal, polycarbonate, any biocompatible synthetic material or combination thereof.

FIG. 13 shows the ease of grip of provided by anchor retaining section 123 and thin flat segment 135.

FIG. 15 shows a detailed view of the fenestration section 111 according to one embodiment. In this embodiment, reinforcement 120 is joined to the side rims 119. The thinner wall 122 is also shown.

FIG. 16 shows a detailed view of a tail anchor retaining section 134b showing the flat segment 135 for grasping and the rounded base 137 for retaining anchor 170. The insertion of the coiled anchor 170 (as shown in FIG. 14) into the rounded base 137 through the flat segment 135 can also bee seen.

Figure 17:
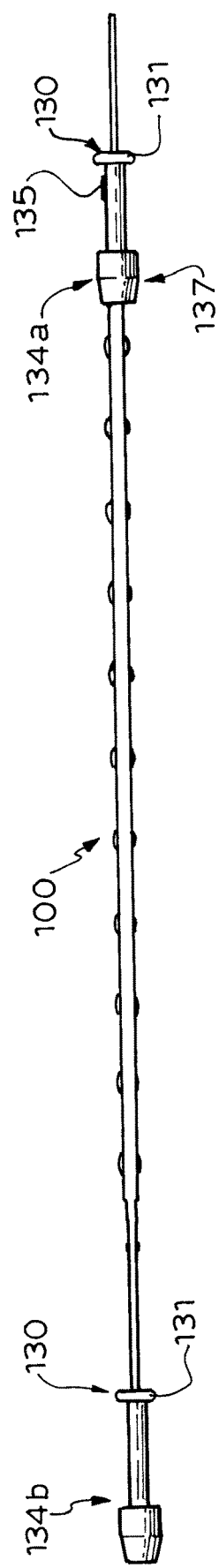
FIG. 17 is a schematic diagram showing a side view of another embodiment of the invention.
Figure 18:
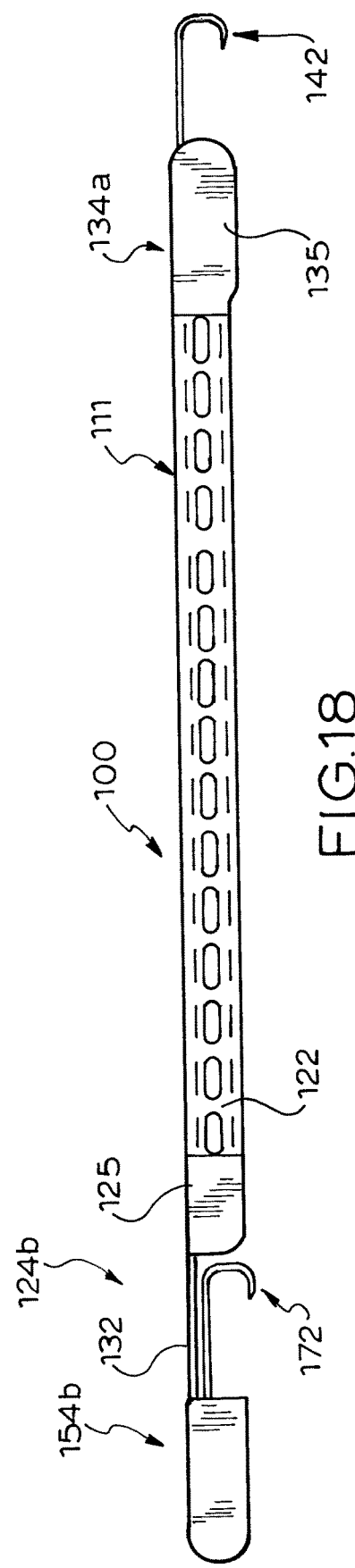
FIG. 18 is a schematic diagram showing a top view of the embodiment shown in FIG. 17.

FIGS. 17 and 18 show a current prototype of device 100. The features of a single leash 132 and stopper branches or protrusions 131 disposed on the anchor retaining sections 134a, 134b are shown. The anchors 140, 170 comprise U-shaped hooks 142, 172 that comprise sharpened ground ends. The hooks 142, 172 are retained as shown with reference to FIGS. 16 and 17.

The embodiment shown in FIG. 17 also lacks a lead spacer 124a, with the fenestration section 111 directly connected to the anchor retaining section 134a. Tail spacer 124b comprises insert 125 and single leash 132.

There are at least two advantages of having anchors 140, 170 oriented in the same direction. First, as the retractor 100 "bends over" above the point where a window is selected, the tail hook 172 is then in the correct orientation to engage with the selected fenestration 112. Second, when removing the device 100 through a 5 mm port, the lead hook 142 may be grasped by a laparoscopic grasper, and withdrawn through the port or trocar. The lead hook 142 will not catch as the point 150 is pointing backwards. As the tail anchor 170 engages within the 5 mm port, because the tail anchor retaining section 134 into which the tail hook 172 is engaged is substantially cylindrical (even though hexagonal) and just smaller than the trocar diameter, the point 180 will still be pointing backwards.

When elongate body 110 comprises two leashes 132 (see FIG. 2). The two leashes 132 extend in parallel and attach to different sides of tail hook 172. When there are two leashes 132 this will help stretch out the seal on the 5 mm port to allow the tail anchor 170 to pass. Even if this does not work with a 5 mm port/trocar due to the seal, it should work with a 5 mm diameter tube inserted through the 5 mm trocar. This is in recognition that the diameters given for laparoscopic trocars generally reflect the size of instruments they accept, not their actual diameter.

These advantages are shown in FIGS. 10A and 10B which illustrate the folding of elongate body 110 so that tail anchor 170 can pass through a fenestration 112 and be secured. By selecting an appropriate fenestration 112a-1, the length of the device 100 can be tailored as required.

In another aspect, the invention provides a method of manufacturing a surgical device 100 for retraction of a body part, the method comprising: forming an elongate body 110 comprising a plurality of fenestrations 112 along a body length wherein each fenestration 112a-1121 is sized to receive at least part of one of the anchors 140, 170; attaching an anchor 140, 170 at each end 102, 104 of the surgical device 100; wherein the surgical device 100 comprises a stopper 130 preventing the tail end 104 of the device 100 being pulled through any of the plurality of fenestrations 112a-1121.

The method for manufacturing the device 100 of the invention may be carried out by using techniques known in the field of silicone injection moulding and surgical needle and/or suture manufacture.

In another aspect of the invention, there is provided a method for inserting device 100 into an incision in a patient, the method comprising the steps of: inserting a surgical trocar into the incision; grasping one anchor 140,170 and inserting it beyond a seal within the trocar, then feeding the elongate body 110 of the device 100 into the trocar, followed by the second anchor 170,140, taking care to avoid a hook 142,172 catching on the seal; inserting the lead anchor 140 onto a first site; straightening out the body 110 of the retractor 100 against the organ to be retracted; and inserting the tail anchor 170 through an appropriate fenestration 112*a*-112*l* along the elongate body 110, and thereon into the site of the second anchorage.

The invention also provides a kit 300 (not shown) comprising the device 100 of the invention and a vacuum retractor. The device of the invention and the vacuum retractor provide complementary retraction.

In this specification, the terms "comprises", "comprising" or similar terms are intended to mean a non-exclusive inclusion, such that an apparatus that comprises a list of elements does not include those elements solely, but may well include other elements not listed.

Throughout the specification the aim has been to describe the invention without limiting the invention to any one embodiment or specific collection of features. Persons skilled in the relevant art may realize variations from the specific embodiments that will nonetheless fall within the scope of the invention.

The claims defining the invention are as follows:

1. A surgical device for retraction of a body part comprising:
    an anchor at each end of the surgical device;
    an elongate body comprising a plurality of fenestrations along a body length wherein each fenestration is sized to receive at least part of one of the anchors;
    a channel comprised in the elongate body, the channel accommodating one of the anchors and the channel extending along part or all of a length between an end of the plurality of fenestrations and an anchor retaining section in which the accommodated anchor is retained within; and
    a stopper preventing a tail end of the device being pulled through any of the plurality of fenestrations.

2. The surgical device of claim 1 wherein the elongate body comprises side rims.

3. The surgical device of claim 1 wherein the elongate body comprises a textured surface or a partially textured surface.

4. The surgical device of claim 1 wherein the plurality of fenestrations is arranged in series along the body length of a fenestration section of the elongate body.

5. The surgical device of claim 1 wherein the elongate body comprises one or more wall between neighbouring one or more fenestrations of the plurality of fenestrations.

6. The surgical device of claim 1 wherein the elongate body comprises one or more spacer between the plurality of fenestrations and the anchors.

7. The surgical device of claim 6 wherein the one or more spacer comprises one or both of an insert and one or more leash.

8. The surgical device of claim 1 wherein the elongate body is sufficiently flexible to fold back or partly fold back on itself to allow at least a part of an anchor to pass through a fenestration.

9. The surgical device of claim 1 wherein the stopper comprises a region of the elongate body or anchor.

10. The surgical device of claim 1 wherein the elongate body comprises one or more wings.

11. The surgical device of claim 1 wherein the elongate body comprises one or more branches.

12. The surgical device of claim 1 wherein the anchor at each end are oriented in a same direction.

13. The surgical device of claim 1 wherein the fenestration includes a reinforcement comprising a bordering section of thickened material.

14. The surgical device of claim 1 wherein the elongate body comprises a strip shape.

15. A method for inserting the surgical device of claim 1 into an incision in a patient, the method comprising the steps of:
    inserting a surgical trocar into the incision;
    grasping a lead anchor and inserting it beyond a seal within the trocar, then feeding the elongate body of the device into the trocar, followed by a tail anchor;
    inserting the lead anchor onto a first site;
    straightening out the body of the retractor against the organ to be retracted; and
    inserting the tail anchor through an appropriate fenestration along the elongate body, and thereon into the site of a second anchorage.

16. A kit comprising the surgical device of claim 1 and a vacuum retractor.

17. A method of manufacturing a surgical device for retraction of a body part, the method comprising:
    forming an elongate body comprising a channel and an anchor retaining section wherein the elongate body comprises a plurality of fenestrations along a body length wherein each fenestration is sized to receive at least part of an anchor, and the channel extends along part or all of a length between an end of the plurality of fenestrations and the anchor retaining section;
    attaching an anchor to each end of the surgical device, one anchor accommodated in the channel; and
    wherein the surgical device comprises a stopper preventing a tail end of the device being pulled through any of the plurality of fenestrations.

* * * * *